(12) United States Patent
Nakazawa

(10) Patent No.: US 7,851,659 B2
(45) Date of Patent: Dec. 14, 2010

(54) METHOD FOR PRODUCING BENZALDEHYDE COMPOUND

(75) Inventor: Koichi Nakazawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/599,042

(22) PCT Filed: May 14, 2008

(86) PCT No.: PCT/JP2008/059289

§ 371 (c)(1),
(2), (4) Date: Nov. 6, 2009

(87) PCT Pub. No.: WO2008/143265

PCT Pub. Date: Nov. 27, 2008

(65) Prior Publication Data

US 2010/0234645 A1   Sep. 16, 2010

(30) Foreign Application Priority Data

May 22, 2007   (JP) .............................. 2007-135065

(51) Int. Cl.
*C07C 45/00* (2006.01)
(52) U.S. Cl. ...................... 568/436; 568/437
(58) Field of Classification Search ................. 568/436, 568/437
See application file for complete search history.

(56) References Cited

U.S. PATENT DOCUMENTS 5,145,980 A    9/1992  Wenderoth et al.
2001/0020110 A1   9/2001  Shintaku et al.

FOREIGN PATENT DOCUMENTS

DE    825547 C    12/1951
JP    2001-316324 A   11/2001
JP    2002-193872 A   7/2002

*Primary Examiner*—Sikarl A Witherspoon
(74) *Attorney, Agent, or Firm*—Panitch Schwarze Belisario & Nadel LLP

(57) ABSTRACT

A method is provided for producing a benzaldehyde compound represented by the formula (2):

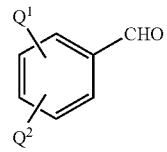

(2)

wherein $Q^1$ and $Q^2$ represent a hydrogen atom etc., including the step of reacting a compound represented by the formula (1):

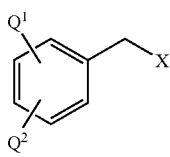

(1)

wherein X represents a chlorine atom etc., and $Q^1$ and $Q^2$ are respectively the same meaning as above, with a secondary nitroalkane and a base in the presence of an alkali metal iodide.

13 Claims, No Drawings

METHOD FOR PRODUCING BENZALDEHYDE COMPOUND

CROSS-REFERENCE TO RELATED APPLICATION

This application is a section 371 of International Application No. PCT/JP2008/059289, filed May 14, 2008, which was published in the Japanese language on Nov. 27, 2008 under International Publication No. WO 2008/143265 A1 and the disclosure of which is incorporated herein by reference.

TECHNICAL FIELD

The present invention relates to a method for producing a benzaldehyde compound.

BACKGROUND ART

U.S. Pat. No. 5,145,980 discloses that benzaldehyde compounds having a phenoxymethyl group are useful as intermediates of bactericide and can be produced by reacting bromomethylbenzonitrile with a phenol compound followed by reducing the obtained mixture.

DE 825547 discloses a method for producing a benzaldehyde compound comprising reacting a benzyl chloride compound with nitrocyclohexane in the presence of sodium ethoxide.

DISCLOSURE OF THE INVENTION

The present invention provides

<1> A method for producing a benzaldehyde compound represented by the formula (2):

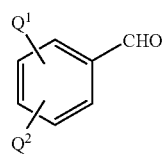

(2)

wherein $Q^1$ and $Q^2$ each independently represent a hydrogen atom; an alkyl group which may be substituted with at least one group selected from the group consisting of an alkoxy group, an alkylthio group, an aryloxy group, an arylthio group, an alkanesulfonyl group which may be substituted with a halogen atom, a benzenesulfonyl group which may be substituted with a nitro group or an alkyl group, and a dialkylamino group which may be substituted with a phenyl group; an alkoxy group which may be substituted with at least one halogen atom; an acyloxy group; an alkanesulfonyloxy group which may be substituted with at least one halogen atom; a benzenesulfonyloxy group which may be substituted with at least one group selected from the group consisting of a nitro group and an alkyl group; a trialkylsilyloxy group; or an aryloxy group which may be substituted with at least one selected from the group consisting of an alkoxy group and a halogen atom (hereinafter, simply referred to as the benzaldehyde compound (2)), comprising reacting a compound represented by the formula (1):

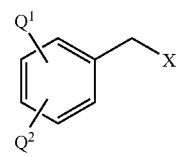

(1)

wherein X represents a fluorine atom, a chlorine atom or a bromine atom, and $Q^1$ and $Q^2$ are respectively the same meaning as above (hereinafter, simply referred to as the compound (1)), with a secondary nitroalkane and a base in the presence of an alkali metal iodide;

<2> The method according to the above <1>, wherein the reaction is conducted by adding the compound (1) to a mixture of the secondary nitroalkane, the base and the alkali metal iodide;

<3> The method according to the above <1> or <2>, wherein the alkali metal iodide is potassium iodide;

<4> The method according to any of the above <1> to <3>, wherein the secondary nitroalkane is 2-nitropropane;

<5> The method according to any of the above <1> to <4>, wherein the base is an alkali metal alkoxide, an alkali metal hydroxide, an alkali metal carbonate or an alkali metal hydrogen carbonate;

<6> The method according to any of the above <1> to <4>, wherein the base is an alkali metal alkoxide;

<7> The method according to the above <5> or <6>, wherein the alkali metal alkoxide is a sodium alkoxide;

<8> The method according to the above <7>, wherein the sodium alkoxide is sodium methoxide or sodium ethoxide;

<9> The method according to any of the above <1> to <8>, wherein $Q^1$ is an alkyl group which may be substituted with at least one group selected from the group consisting of an alkoxy group, an alkylthio group, an aryloxy group, an arylthio group, an alkanesulfonyl group which may be substituted with a halogen atom, a benzenesulfonyl group which may be substituted with a nitro group or an alkyl group, and a dialkylamino group which may be substituted with a phenyl group;

<10> The method according to any of the above <1> to <8>, wherein $Q^1$ is an alkyl group which may be substituted with an aryloxy group;

<11> The method according to the above <9> or <10>, wherein the alkyl group which may be substituted with an aryloxy group is a 2,5-dimethylphenoxymethyl group;

<12> The method according to any of the above <1> to <11>, wherein $Q^1$ is bonded at ortho-position to the methyl group substituted with X;

<13> The method according to any of the above <1> to <12>, wherein $Q^2$ is a hydrogen atom; and the like.

BEST MODE FOR CARRYING OUT THE PRESENT INVENTION

In the formula of the compound (1), X represents a fluorine atom, a chlorine atom or a bromine atom, and $Q^1$ and $Q^2$ each independently represent a hydrogen atom; an alkyl group which may be substituted with at least one group selected from the group consisting of an alkoxy group, an alkylthio group, an aryloxy group, an arylthio group, an alkanesulfonyl group which may be substituted with a halogen atom, a benzenesulfonyl group which may be substituted with a nitro group or an alkyl group, and a dialkylamino group which may be substituted with a phenyl group; an alkoxy group which may be substituted with at least one halogen atom; an acyloxy group; an alkanesulfonyloxy group which may be substituted with at least one halogen atom; a benzenesulfonyloxy group which may be substituted with at least one group selected from the group consisting of a nitro group and an alkyl group; a trialkylsilyloxy group; or an aryloxy group which may be substituted with at least one selected from the group consisting of an alkoxy group and a halogen atom.

Examples of the alkyl group include a C1-C6 alkyl group such as a methyl group, an ethyl group, a propyl group, an isopropyl group, a butyl group, an isobutyl group, a tert-butyl group, a pentyl group and a hexyl group.

Examples of the alkoxy group include a C1-C4 alkoxy group such as a methoxy group, an ethoxy group, a propoxy group and a butoxy group. Examples of the alkylthio group include a C1-C4 alkylthio group such as a methylthio group, an ethylthio group, a propylthio group and a butylthio group.

Examples of the aryloxy group include a C6-C12 aryloxy group such as a phenoxy group and a 2,5-dimethylphenoxy group. Examples of the arylthio group include a C6-C12 arylthio group such as a phenylthio group and a 2,5-dimethylphenylthio group.

Examples of the alkanesulfonyl group which may be substituted with a halogen atom include an unsubstituted C1-C4 alkanesulfonyl group such as a methanesulfonyl group and C1-C4 alkanesulfonyl group substituted with a halogen atom (for example, a fluorine atom) such as a trifluoromethanesulfonyl group. Examples of the benzenesulfonyl group which may be substituted with a nitro group or an alkyl group include an unsubstituted benzenesulfonyl group, a benzenesulfonyl group substituted with a C1-C4 alkyl group such as a p-toluenesulfonyl group and a benzenesulfonyl group substituted with a nitro group such as an o-nitrobenzenesulfonyl group and a p-nitrobenzenesulfonyl group.

Examples of the dialkylamino group which may be substituted with a phenyl group include a dimethylamino group, a diethylamino group, a dipropylamino group, a diisopropylamino group, a benzylmethylamino group and a dibenzylamino group.

Specific examples of the alkyl group which may be substituted with at least one group selected from the group consisting of an alkoxy group, an alkylthio group, an aryloxy group, an arylthio group, an alkanesulfonyl group which may be substituted with a halogen atom, a benzenesulfonyl group which may be substituted with a nitro group or an alkyl group, and a dialkylamino group which may be substituted with a phenyl group include a methyl group, an ethyl group, a propyl group, an isopropyl group, a butyl group, an isobutyl group, a tert-butyl group, a pentyl group, a hexyl group, a methoxymethyl group, an ethoxymethyl group, a methylthiomethyl group, a phenylthiomethyl group, a 2,5-dimethylphenoxymethyl group, a methanesulfonylmethyl group, a chloromethanesulfonylmethyl group, a trifluoromethanesulfonylmethyl group, a 4-benzenesulfonylmethyl group, a (p-nitrobenzenesulfonyl)methyl group, a dimethylaminomethyl group, a diethylaminomethyl group, a diisopropylaminomethyl group, a dibenzylaminomethyl group, a 2-methoxyethyl group, a 2-ethoxyethyl group, a 2-methylthioethyl group, a 2-phenylthioethyl group, a 2-methanesulfonylethyl group, a 2-trifluoromethanesulfonylethyl group, a 2-benzenesulfonylethyl group, a 2-(p-nitrobenzenesulfonylethyl) group, a 2-dimethylaminoethyl group, a 2-diethylaminoethyl group, a 2-diisopropylaminoethyl group and a 2-dibenzylaminoethyl group.

Examples of the alkoxy group which may be substituted with at least one halogen atom include an unsubstituted C1-C4 alkoxy group such as a methoxy group, an ethoxy group, a propoxy group, an isopropoxy group and a butoxy group, and C1-C4 alkoxy group substituted with at least one halogen atom (for example, a fluorine atom) such as a fluoromethoxy group, a difluoromethoxy group, a trifluoromethoxy group, a pentafluoroethoxy group and a 2-trifluoromethyl-3,3,3-trifluoropropoxy group.

Examples of the acyloxy group include a C2-C15 acyloxy group such as an acetoxy group, a propionyloxy group, a butyryloxy group, a pivaloyloxy group, a neopentanecarbonyloxy group, a benzoyloxy group, a naphthoyloxy group, a phenylacetoxy group and a naphthylacetoxy group.

Examples of the alkanesulfonyloxy group which may be substituted with at least one halogen atom include an unsubstituted C1-C4 alkanesulfonyloxy group such as a methanesulfonyloxy group and an ethanesulfonyloxy group, and a C1-C4 alkanesulfonyloxy group substituted with at least one halogen atom (for example, a fluorine atom) such as trifluoromethanesulfonyloxy group.

Examples of the benzenesulfonyloxy group which may be substituted with at least one group selected from the group consisting of a nitro group and an alkyl group include an unsubstituted benzenesulfonyloxy group, a benzenesulfonyloxy group substituted with a C1-C4 alkyl group such as a p-toluenesulfonyloxy group and a benzenesulfonyloxy group substituted with a nitro group such as an o-nitrobenzenesulfonyloxy group and a p-nitrobenzenesulfonyloxy group.

Examples of the trialkylsilyloxy group include a C3-C12 trialkylsilyloxy group such as a trimethylsilyloxy group, a triethylsilyloxy group, a tripropylsilyloxy group and a tert-butyldimethylsilyloxy group.

Examples of the aryloxy group which may be substituted with at least one selected from the group consisting of an alkoxy group and a halogen atom include an unsubstituted C6-C20 aryloxy group such as a phenoxy group, a naphthyloxy group, a 4-methylphenoxy group, a 2-methylphenoxy group, a 2,4-dimethylphenoxy group and a 2,4-di-tert-butylphenoxy group, a C6-C20 aryloxy group substituted with a C1-C4 alkoxy group such as a 4-methoxyphenoxy group and a 4-ethoxyphenoxy group, and a C6-C20 aryl group substituted with at least one halogen atom (for example, a fluorine atom) such as a 2-fluorophenoxy group, a 4-fluorophenoxy group and a pentafluorophenoxy group.

Examples of the compound (1) include benzyl chloride, 2-methylbenzyl chloride, 4-methylbenzyl chloride, 2-ethylbenzyl chloride, 2-isopropylbenzyl chloride, 4-tert-butylbenzyl chloride, 2-(methoxymethyl)benzyl chloride, 2-(2-methoxyethyl)benzyl chloride, 2-(ethoxymethyl)benzyl chloride, 2-(methylthiomethyl)benzyl chloride, 2-(2-methylthioethyl) benzyl chloride, 2-(ethylthiomethyl)benzyl chloride, 2-(phenoxymethyl)benzyl chloride, 2-(2,5-dimethylphenoxymethyl)benzyl chloride, 4-(2,5-dimethylphenoxymethyl) benzyl chloride, 2-(phenylthiomethyl)benzyl chloride, 2-(2, 5-dimethylphenylthiomethyl)benzyl chloride, 2-(methanesulfonylmethyl)benzyl chloride, 2-(trifluoromethanesulfonylmethyl)benzyl chloride, 2-(benzenesulfonylmethyl)benzyl chloride, 2-(p-toluenesulfonylmethyl)benzyl chloride, 2-(o-nitrobenzenesulfonylmethyl)benzyl chloride, 2-(dimethylaminomethyl)benzyl chloride, 2-(2-dimethylaminoethyl)benzyl chloride, 2-(dibenzylaminomethyl)benzyl chloride, 2-methoxybenzyl chloride, 3-methoxybenzyl chloride, 4-methoxybenzyl chloride, 2-ethoxybenzyl chloride, 2-isopropoxybenzyl chloride, 2-difluoromethoxybenzyl chloride, 2-trifluoromethoxybenzyl chloride, 2-pentafluoroethoxybenzyl chloride, 2-(2-fluoromethyl-3,3,3-trifluoropropoxy)benzyl chloride, 2-acetoxybenzyl chloride, 4-acetoxybenzyl chloride, 2-(propionyloxy) benzyl chloride, 2-(butyryloxy)benzyl chloride, 2-(pivaloyloxy)benzyl chloride, 2-(phenylacetoxy)benzyl chloride, 4-(phenylacetoxy)benzyl chloride, 2-(naphthylacetoxy)benzyl chloride, 2-(methanesulfonyloxy)benzyl chloride, 2-(trifluoromethanesulfonyloxy)benzyl chloride, 2-(p-toluenesulfonyloxy)benzyl chloride, 2-(o-nitrobenzenesulfonyloxy)benzyl chloride, 2-(p-nitrobenzenesulfonyloxy)benzyl chloride, 2-trimethylsilyloxybenzyl chloride, 2-triethylsilyloxybenzyl chloride, 2-tripropylsilyloxybenzyl chloride, 2-tert-butyldimethylsilyloxybenzyl chloride, 2-phenoxybenzyl chloride, 3-phenoxybenzyl chloride, 2-naphthyloxybenzyl chloride, 2-(4-methylphenoxy)benzyl chloride, 2-(2-methylphenoxy)benzyl chloride, 2-(2,4-dimethylphenoxy) benzyl chloride, 2-(2,4-di-tert-butylphenoxy)benzyl chloride, 2-(4-methoxyphenoxy)benzyl chloride, 2-(4-ethoxyphenoxy)benzyl chloride, 2-(2-fluorophenoxy)benzyl chloride, 2-(4-fluorophenoxy)benzyl chloride, 2-pentafluorophenoxybenzyl 2-(2,6-dimethylphenoxymethyl)-4-methoxymethylbenzyl chloride, 2-(2,6-dimethylphenoxymethyl)-4-(methylthiomethyl)benzyl chloride, 2-(2,6-dimethylphenoxymethyl)-4-(phenylthiomethyl)benzyl chloride, 2-(2,6-dimethylphenoxymethyl)-4-(dimethylaminomethyl)benzyl chloride, 2-(2,6-dimethylphenoxymethyl)-4-trifluoromethoxybenzyl chloride, 2-(2,6-dimethylphenoxymethyl)-4-pentafluoroethoxybenzyl chloride, 2-(2,6-dimethylphenoxymethyl)-4-acetoxybenzyl chloride, 2-(2,6-dimethylphenoxymethyl)-4-benzoyloxybenzyl chloride, 2-(2,6-dimethylphenoxymethyl)-4-(trimethylsilyloxy)benzyl chloride, 2-(2,6-dimethylphenoxymethyl)-4-(triethylsilyloxy)benzyl chloride, 2-(2,6-dimethylphenoxymethyl)-4-(tert-butyldimethylsilyloxy) benzyl chloride, 2-(2,6-dimethylphenoxymethyl)-4-phenoxybenzyl chloride, 2-(2,6-dimethylphenoxymethyl)-4-pentafluorophenoxybenzyl chloride and each of the above-mentioned compounds in which "benzyl chloride" is replaced with "benzyl fluoride" or "benzyl bromide".

As the compound (1), commercially available one may be used and may be produced according to any known methods to be used.

Examples of the secondary nitroalkane include a C3-C6 secondary nitroalkane such as 2-nitropropane, 2-nitrobutane, 3-nitrobutane and nitrocyclohexane, and 2-nitropropane is preferable. As the secondary nitroalkane, commercially available one is usually used as it is.

The used amount of the secondary nitroalkane is usually, 1 mole or more per 1 mole of the compound (1), and while there is no specific upper limit, it is preferably 1 to 3 moles.

Examples of the base include alkali metal alkoxides such as sodium methoxide, sodium ethoxide and potassium tert-butoxide, alkali metal hydroxides such as lithium hydroxide, sodium hydroxide and potassium hydroxide, alkali metal carbonates such as sodium carbonate, potassium carbonate and lithium carbonate, alkali metal hydrogen carbonates such as sodium hydrogen carbonate, potassium hydrogen carbonate and lithium hydrogen carbonate, and alkali metal hydrides such as sodium hydride, potassium hydride and lithium hydride. Among them, alkali metal alkoxides are preferable and a sodium alkoxide is more preferable, and sodium methoxide and sodium ethoxide are especially preferable. The used amount of the base is usually 1 mole or more per 1 mole of the secondary nitroalkane, and while there is no specific upper limit, it is preferably 1 to 3 moles.

Examples of the alkali metal iodide include potassium iodide, sodium iodide and lithium iodide, and potassium iodide is preferable. As the alkali metal iodide, commercially available one is usually used. The used amount thereof is usually 0.01 mole or more per 1 mole of the compound (1), and while there is no specific upper limit, it is preferably 0.03 to 3 moles.

The reaction is usually carried out in the presence of a solvent. Examples of the solvent include aromatic hydrocarbon solvents such as xylene, toluene, chlorobenzene and benzene, aliphatic hydrocarbon solvents such as pentane, hexane, heptane and cyclohexane, ether solvents such as tetrahydrofuran, diethyl ether, tert-butyl methyl ether and cyclopentyl methyl ether, and alcohol solvents such as methanol, ethanol, 2-propanol and tert-butanol. These may be used alone and two or more kinds thereof may be mixed to be used. A mixed solvent of the alcohol solvent and the aromatic hydrocarbon solvent is preferable and a mixed solvent of methanol and toluene is more preferable. While the used amount of the solvent is not particularly limited, it is usually 100 parts by weight or less per 1 part by weight of the compound (1) from the viewpoint of economic efficiency.

The reaction temperature is usually −5° C. or more and a boiling point of the solvent or less, and preferably 5 to 70° C.

The reaction may be conducted under a normal pressure and under pressure.

The progress of the reaction can be checked by a conventional analytical means such as gas chromatography, high performance liquid chromatography and NMR.

The reaction is carried out by mixing the compound (1), the secondary nitroalkane, the base and the alkali metal iodide. While the mixing order is not particularly limited, the reaction is preferably conducted by mixing the secondary nitroalkane, the base and the alkali metal iodide, adjusting the obtained mixture to predetermined temperature followed by adding the compound (1) to the mixture.

The benzaldehyde compound (2) can be isolated, for example, by filtrating the obtained mixture followed by concentration. The isolated benzaldehyde compound (2) may be further purified by a conventional purification means such as recrystallization, distillation and column chromatography.

Examples of the benzaldehyde compound (2) include 2-methylbenzaldehyde, 4-methylbenzaldehyde, 2-ethylbenzaldehyde, 2-isopropylbenzaldehyde, 4-tert-butylbenzaldehyde, 2-(methoxymethyl)benzaldehyde, 2-(2-methoxyethyl) benzaldehyde, 2-(ethoxymethyl)benzaldehyde, 2-(methylthiomethyl)benzaldehyde, 2-(2-methylthioethyl) benzaldehyde, 2-(ethylthiomethyl)benzaldehyde, 2-(phenoxymethyl)benzaldehyde, 2-(2,5-dimethylphenoxymethyl) benzaldehyde, 4-(2,5-dimethylphenoxymethyl) benzaldehyde, 2-(phenylthiomethyl)benzaldehyde, 2-(2,5-dimethylphenylthiomethyl)benzaldehyde, 2-(methanesulfonylmethyl)benzaldehyde, 2-(trifluoromethanesulfonylmethyl)benzaldehyde, 2-(benzenesulfonylmethyl)benzaldehyde, 2-(p-toluenesulfonylmethyl)benzaldehyde, 2-(o-nitrobenzenesulfonylmethyl)benzaldehyde, 2-(dimethylaminomethyl)benzaldehyde, 2-(2-dimethylaminoethyl)benzaldehyde, 2-(dibenzylaminomethyl)benzaldehyde, 2-methoxybenzaldehyde, 3-methoxybenzaldehyde, 4-methoxybenzaldehyde, 2-ethoxybenzaldehyde, 2-isopropoxybenzaldehyde, 2-difluoromethoxybenzaldehyde, 2-trifluoromethoxybenzaldehyde, 2-pentafluoroethoxybenzaldehyde, 2-(2-fluoromethyl-3,3,3-trifluoropropoxy) benzaldehyde, 2-acetoxybenzaldehyde, 4-acetoxybenzaldehyde, 2-propionyloxybenzaldehyde, 2-butyryloxybenzaldehyde, 2-pivaloyloxybenzaldehyde, 2-(phenylacetoxy)benzaldehyde, 4-(phenylacetoxy)benzaldehyde, 2-(naphthylacetoxy)benzaldehyde, 2-(methanesulfonyloxy)benzaldehyde, 2-(trifluoromethanesulfonyloxy)benzaldehyde, 2-(p-toluenesulfonyloxy)benzaldehyde, 2-(o-nitrobenzenesulfonyloxy)benzaldehyde, 2-(p-nitrobenzenesulfonyloxy)benzaldehyde, 2-trimethylsilyloxybenzaldehyde, 2-triethylsilyloxybenzaldehyde, 2-tripropylsilyloxybenzaldehyde, 2-tert-butyldimethylsilyloxybenzaldehyde, 2-phenoxybenzaldehyde, 3-phenoxybenzaldehyde, 2-naphthyloxybenzaldehyde, 2-(4-methylphenoxy)benzaldehyde, 2-(2-methylphenoxy)benzaldehyde, 2-(2,4-dimethylphenoxy)benzaldehyde, 2-(2,4-di-tert-butylphenoxy)benzaldehyde, 2-(4-methoxyphenoxy)benzaldehyde, 2-(4-ethoxyphenoxy)benzaldehyde, 2-(2-fluorophenoxy)benzaldehyde, 2-(4-fluorophenoxy)benzaldehyde, 2-pentafluorophenoxybenzaldehyde, 2-(2,6-dimethylphenoxymethyl)-4-(methoxymethyl)benzaldehyde, 2-(2,6-dimethylphenoxymethyl)-4-(methylthiomethyl)benzaldehyde, 2-(2,6-dimethylphenoxymethyl)-4-(phenylthiomethyl)benzaldehyde, 2-(2,6-dimethylphenoxymethyl)-4-(dimethylaminomethyl)benzaldehyde, 2-(2,6-dimethylphenoxymethyl)-4-trifluoromethoxybenzaldehyde, 2-(2,6-dimethylphenoxymethyl)-4-pentafluoroethoxybenzaldehyde, 2-(2,6-dimethylphenoxymethyl)-4-acetoxybenzaldehyde, 2-(2,6-dimethylphenoxymethyl)-4-benzoyloxybenzaldehyde, 2-(2,6-dimethylphenoxymethyl)-4-trimethylsilyloxybenzaldehyde, 2-(2,6-dimethylphenoxymethyl)-4-triethylsilyloxybenzaldehyde, 2-(2,6-dimethylphenoxymethyl)-4-(tert-butyldimethylsilyloxy)benzaldehyde, 2-(2,6-dimethylphenoxymethyl)-4-phenoxybenzaldehyde and 2-(2,6-dimethylphenoxymethyl)-4-pentafluorophenoxybenzaldehyde.

EXAMPLES

The present invention is illustrated in more detail by Examples below. The present invention is not limited to these Examples. The analysis was conducted by high performance liquid chromatography internal standard method.

Example 1

Into a 200 mL round-bottomed flask, 7.8 g of 2-nitropropane (purity: 98%), 0.6 g of potassium iodide and 40.0 g of methanol were charged to adjust an inner temperature to 10° C. To the obtained mixture, 15.3 g of 28% by weight sodium methoxide/methanol solution was added dropwise. The obtained mixture was stirred at room temperature for 30 minutes, and then, adjusted at 40° C. To the mixture, a mixture of 20.0 g of 2-(2,5-dimethylphenoxymethyl)benzyl chloride (content: 93.4% by weight) and 60 g of toluene was added dropwise over 3 hours. After completion of the addition, the obtained mixture was stirred at the same temperature for 12 hours. The obtained reaction mixture was filtrated. The filtrate was concentrated until an inner temperature became a boiling point of methanol or more. The obtained concentrated residue was washed with 60.0 g of 10% by weight aqueous sodium hydroxide solution to obtain an organic layer and an aqueous layer. The aqueous layer was extracted with 40.0 g of toluene to obtain a toluene layer. The toluene layer was mixed with the previously obtained organic layer to wash with 40.0 g of water. The organic layer after washing was concentrated under reduced pressure to obtain 17.6 g of a yellow solid containing 2-(2,5-dimethylphenoxymethyl)benzaldehyde. Content: 95.2% by weight. Yield: 97%.

Comparative Example

According to the same manner as that described in Example 1,2-(2,5-dimethylphenoxymethyl)benzaldehyde was obtained except that potassium iodide was not used and stirring time after completion of the addition of a mixture of 2-(2,5-dimethylphenoxymethyl)benzyl chloride and toluene was 40 hours. Yield: 87%.

Example 2

Into a 200 mL round-bottomed flask, 7.8 g of 2-nitropropane (purity: 98%), 0.6 g of potassium iodide and 40.0 g of methanol were charged to adjust an inner temperature to 10° C. To the obtained mixture, 15.3 g of 28% by weight sodium methoxide/methanol solution was added dropwise. The obtained mixture was stirred at room temperature for 30 minutes, and then, a mixture of 20.0 g of 2-(2,5-dimethylphenoxymethyl)benzyl chloride (content: 93.4% by weight) and 60 g of methanol was added dropwise thereto over 3 hours. After completion of the addition, the obtained mixture was stirred at an inner temperature of 40° C. for 4 hours. The obtained reaction mixture was filtrated. The filtrate was concentrated under reduced pressure, and then, the concentrated residue was diluted with 60.0 g of toluene. The obtained solution was washed with 60.0 g of 10% by weight aqueous sodium hydroxide solution to obtain an organic layer and an aqueous layer. The aqueous layer was extracted with 40.0 g of toluene to obtain a toluene layer. The toluene layer was mixed with the previously obtained organic layer to wash with 40.0 g of water. The organic layer after washing was concentrated under reduced pressure to obtain 18.2 g of a pale yellow solid containing 2-(2,5-dimethylphenoxymethyl)benzaldehyde. Content: 91.5% by weight. Yield: 97%.

INDUSTRIAL APPLICABILITY

According to the present invention, a benzaldehyde compound, which is useful as an intermediate of bactericide, can be obtained.

The invention claimed is:

1. A method for producing a benzaldehyde compound represented by the formula (2):

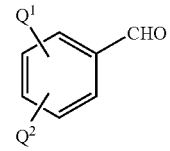

wherein $Q^1$ and $Q^2$ each independently represent a hydrogen atom; an alkyl group which may be substituted with at least one group selected from the group consisting of an alkoxy group, an alkylthio group, an aryloxy group, an arylthio group, an alkanesulfonyl group which may be substituted with a halogen atom, a benzenesulfonyl group which may be substituted with a nitro group or an alkyl group, and a dialkylamino group which may be substituted with a phenyl group; an alkoxy group which may be substituted with at least one halogen atom; an acyloxy group; an alkanesulfonyloxy group which may be substituted with at least one halogen atom; a benzenesulfonyloxy group which may be substituted with at least one group selected from the group consisting of a nitro group and an alkyl group; a trialkylsilyloxy group; or an aryloxy group which may be substituted with at least one selected from the group consisting of an alkoxy group and a halogen atom, comprising reacting a compound represented by the formula (1):

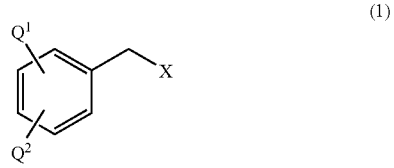

wherein X represents a fluorine atom, a chlorine atom or a bromine atom, and $Q^1$ and $Q^2$ are respectively the same meaning as above, with a secondary nitroalkane and a base in the presence of an alkali metal iodide.

2. The method according to claim 1, wherein the reaction is conducted by adding the compound represented by the formula (1) to a mixture of the secondary nitroalkane, the base and the alkali metal iodide.

3. The method according to claim 1, wherein the alkali metal iodide is potassium iodide.

4. The method according to claim 1, wherein the secondary nitroalkane is 2-nitropropane.

5. The method according to claim 1, wherein the base is an alkali metal alkoxide, an alkali metal hydroxide, an alkali metal carbonate or an alkali metal hydrogen carbonate.

6. The method according to claim 1, wherein the base is an alkali metal alkoxide.

7. The method according to claim 6, wherein the alkali metal alkoxide is a sodium alkoxide.

8. The method according to claim 7, wherein the sodium alkoxide is sodium methoxide or sodium ethoxide.

9. The method according to claim 1, wherein $Q^1$ is an alkyl group which may be substituted with at least one group selected from the group consisting of an alkoxy group, an alkylthio group, an aryloxy group, an arylthio group, an alkanesulfonyl group which may be substituted with a halogen atom, a benzenesulfonyl group which may be substituted with a nitro group or an alkyl group, and a dialkylamino group which may be substituted with a phenyl group.

10. The method according to claim 1, wherein $Q^1$ is an alkyl group which may be substituted with an aryloxy group.

11. The method according to claim 10, wherein the alkyl group which may be substituted with an aryloxy group is a 2,5-dimethylphenoxymethyl group.

12. The method according to claim 1, wherein $Q^1$ is bonded at ortho-position to the methyl group substituted with X.

13. The method according to claim 1, wherein $Q^2$ is a hydrogen atom.

* * * * *